United States Patent [19]

McDaniel

[11] Patent Number: 5,648,593
[45] Date of Patent: *Jul. 15, 1997

[54] STRESS TOLERANT PYRETHRUM PLANTS

[75] Inventor: Robert G. McDaniel, Tucson, Ariz.

[73] Assignee: Arizona Board of Regents, on behalf of the University of Arizona, Tucson, Ariz.

[ * ] Notice: The term of this patent shall not extend beyond the expiration date of Pat. No. P.P. 07,495.

[21] Appl. No.: 321,372

[22] Filed: Oct. 11, 1994

Related U.S. Application Data

[63] Continuation of Ser. No. 21,308, Feb. 22, 1993, abandoned, which is a continuation-in-part of Ser. No. 680,989, Apr. 5, 1991, abandoned, which is a continuation of Ser. No. 332,611, Mar. 31, 1989, Pat. No. Plant 7,495.

[51] Int. Cl.$^6$ .................... A01H 1/04; A01H 4/00; A01H 5/02; C12N 5/04
[52] U.S. Cl. .................. 800/200; 800/250; 800/255; 800/DIG. 12; Plt./74.1; 47/58; 47/DIG. 1
[58] Field of Search ................... 800/200, 205, 800/250, 255, DIG. 12; 435/172.1, 172.2, 172.3, 240.4, 240.49; 560/124; Plt./74.1; 47/58, DIG. 1

[56] References Cited

U.S. PATENT DOCUMENTS

| P.P. 5,848 | 1/1987 | Bhat et al. | Plt./74.1 |
| P.P. 7,495 | 4/1991 | McDaniel | Plt./74.1 |

OTHER PUBLICATIONS

Khalid et al. 1989. Sci Hortic (Amst). 38(3–4). pp. 287–294. (abstract).
Laurie et al. 1969. In Commercial Flower Forcing. pp. 282–285. McGraw-Hill Book Company.
Pal et al. 1985. Pyrethrum Post. 16(1). pp. 3–11.
Nelson. 1975. In Pyrethrum Flowers. pp. 86–97.
Parlevliet. 1974. Euphytica. 23(2). pp. 377–384.
Huxley et al. (ed.). 1992. In Dictionary of Gardening. vol. 4. R to Z. pp. 433—The New Royal Horticultural Society.
Zieg et al. 1983. Planta Med. 48(2). pp. 88–91. (abstract).
Huxley et al. 1992. The New Royal Horticultural Society Directory of Gardening p. 433.
Note: A copy of this publication was mailed with the previous office Action (paper #2), but the reference was inadvertently left off of the Form PTO–892. Another copy of the reference is being supplied with this Office Action in case the Applicant separated the original copy from the file.

*Primary Examiner*—Gary Benzion
*Assistant Examiner*—Erich E. Veitenheimer
*Attorney, Agent, or Firm*—Ogram & Teplitz, P.C.

[57] ABSTRACT

New and distinct varieties of *Chrysanthemum cinerariaefolium* plants exhibit environmental stress tolerance over a temperature range extending as low as about 17° F. and as high as about 115° F., and are also capable of producing flowers having an endogenous pyrethrin content of at least about 1.5%. The new varieties include both triploid plants which are largely sterile, and diploid plants which exhibit good cross fertility.

23 Claims, 6 Drawing Sheets
(6 of 6 Drawing(s) in Color)

STRESS TOLERANT PYRETHRUM PLANTS

This is a continuation of application Ser. No. 08/021,308, filed Feb. 22, 1993, now abandoned, which in turn is a continuation-in-part of application Ser. No. 07/680,989, filed Apr. 5, 1991, now abandoned, which in turn is a continuation of application Ser. No. 07/332,611, filed Mar. 31, 1989, now Plant Patent No. 7,495, issued Apr. 9, 1991.

BACKGROUND OF THE INVENTION

This invention relates to pyrethrum plants and, more particularly, to novel varieties of pyrethrum plants characterized by high pyrethrin content combined with environmental stress tolerance.

The flowers of *Chrysanthemum cinerariaefolium*, commonly known as pyrethrum, yield a family of six related secondary metabolites, collectively called pyrethrin, which exhibits excellent insecticidal properties. Pyrethrin has become a commercially important insecticide due to the fact that it has minimal mammalian toxicity, it photodegrades rapidly leaving no toxic residue in the environment, and it is highly effective against target organisms. It is the insecticide of choice for use in food manufacturing and in stable, dairy barn and pet fly and other insect control.

Economical commercial production of pyrethrin from *Chrysanthemum cinerariaefolium* requires plants whose flowers have a relatively high endogenous pyrethrin content, i.e., at least about 1.5%, and preferably about 2.0% or higher, by weight of dried flowers. Heretofore, such high levels of pyrethrin content have been reproducibly achievable only with *Chrysanthemum cinerariaefolium* grown in those parts of the world enjoying a relatively temperate climate with little or no frost and no excessive heat. The reason for this is the inverse correlation that has generally been found to exist between the vigor of this plant and its pyrethrin content. Thus, pyrethrin content is normally highest in the least thrifty and least vigorous plants, while those plants which do survive for a time in harsh climates have little or nearly no pyrethrin content. Consequently, commercial pyrethrin production has for the most part been limited to areas of the world either near the equator and at elevations sufficiently high so as to avoid heat stress while not so high as to encounter frost, or where tropical heat encountered at low elevations is moderated by coastal climatic effects.

Based on the foregoing, it has come to be generally accepted by *Chrysanthemum cinerariaefolium* growers and breeders that any variety of this plant having a relatively high level of pyrethrin content, would necessarily lack the environmental stress tolerance sufficient for long-term survival under the climatic extremes of both frost and excessive heat.

SUMMARY OF THE INVENTION

The present invention is directed to new and distinct varieties of *Chrysanthemum cinerariaefolium* which exhibit environmental stress tolerance over a temperature range extending as low as about 17° F. and as high as about 115° F., and which are capable of producing flowers having an endogenous pyrethrin content of at least about 1.5%, and preferably at least about 2.0%, by weight of dried flowers. The plants of the present invention are also characterized by substantially synchronous and substantially planar flowering habit and substantially erect growth with low lodging tendency. The flowers of the plants preferably have a pyrethrin I to pyrethrin II ratio of at least 1.

The new varieties include both triploid and diploid plants. The triploid plants are largely sterile, and are readily asexually reproducible from splits or cuttings. The diploid plants exhibit good cross fertility, and are reproducible either asexually from splits or cuttings, or sexually from seed.

DESCRIPTION OF PREFERRED EMBODIMENTS

The new and distinct varieties of *Chrysanthemum cinerariaefolium* in accordance with the present invention, are the result of a recurrent selection breeding program started in 1979 from *Chrysanthemum cinerariaefolium* seed of unknown origin, and having the objective of creating new *Chrysanthemum cinerariaefolium* cultivars with the combined characteristics of high pyrethrin content and environmental stress tolerance. The breeder stock is held by the University of Arizona, College of Agriculture, Department of Plant Sciences, Tucson, Ariz.

Breeding Methodology

*Chrysanthemum cinerariaefolium* seed of unknown origin was germinated and grown in a greenhouse. In 1980, vigorous transplants were chosen from the greenhouse grown nursery stock and transplanted to a field at the University of Arizona, Mararia Agricultural Center. Over 99% of the transplants failed to survive the combination of the high summer temperatures (daytime temperatures ranging from about 95° F. to about 115° F.), exhibiting crown rots associated with high night temperatures (ranging from about 80° F. to about 100° F.); the sub-freezing winter nights; and the need to exhibit a measure of drought tolerance between scheduled irrigations. Some of the survivors set seed which was outcrossed, as *Chrysanthemum cinerariaefolium* is self-incompatible.

The seed from the surviving plants was harvested, germinated in a growth chamber, and transplanted to the greenhouse. The young plants were transplanted to an adjacent field area to establish a second field test and grown in 24" row spacings on cotton beds with 40" centers. After over one year in the field, the best of the second generation plants were split into several pieces. These asexual propagules were planted in rows and used to evaluate the phenotypes of the plants. Phenotypes which exhibited a planar flowering habit, lodging resistance and ease of picking were selected. All breeding lines were evaluated for pyrethrin content and quality, determined by the relative proportion of the six distinct chemical components of pyrethrin.

Likely, due to the extreme climatic stresses at the Marana field, some of the clones showed a biannual tendency. Because of this and other field conditions at that location which made continued growth undesirable, the most promising asexual propagules, their seed and some seedling plants were then transplanted over a period of time to the University of Arizona Campus Agricultural Center in 1983 in three adjacent field areas A, B and C. In 1984 and 1985 the best of these materials, sister lines grown from seed and asexual propagules from the greenhouse were transplanted to a new field area D. Phenotypes and pyrethrin content and quality were evaluated annually.

To test the stress tolerance of the plants to high temperatures and salinated soil, in 1981 seedlings from the greenhouse were transplanted to a field plot that was established at the University of Arizona, Safford Agricultural Center. These clones were irrigated with salinated water which resulted in soil salinity levels approaching ⅓ that of sea water. Survival rates of these transplants were extremely low and the plants were badly stunted. Pyrethrin levels were lower than desired.

All surviving clones from the Safford field were transplanted back to the University of Arizona Campus Agricultural Center in 1985 in a new field area E, and seed from the most promising "salt tolerant" clones were replicated in 30 foot half sib progeny tests.

At the same time 29 rows were planted in a new field area F at the University of Arizona Campus Agricultural Center. Each of these twenty-nine rows were divided into seven, thirty foot sections. Seed from the most promising clones growing in field areas A through D were sown head-to-row in randomized duplicate replications within field area F. Field area F was divided into three subplots with randomizations within each sub-plot. Rows 1 through 6 were half sib progeny of clones which displayed excellent lodging resistance, but on which pyrethrin content data were incomplete at planting time. Rows 7 through 21 comprised half sib progeny whose parent clones exhibited good lodging resistance, planar flowering habit and a relatively high pyrethrin content compared to the base population. Rows 22 through 29 were half sib progeny of other promising clones, and seed from all other promising clones as well as four entries comprising a composite "bulk" of seed from all field F entries. After one season, the three top pyrethrin producing plants from field area D were split and established in 30 foot areas of field area F to enable evaluation of pyrethrin levels from genetically identical clones. Pyrethrin content was determined over a four year period on selected plants from field area F.

At the end of the four year period, two rows at each side of field area F were abandoned, and the best plants from each of those four rows together with some superior greenhouse grown plants were transplanted into areas of the field where stands had thinned. The resulting field then became labelled as field area G.

Field area H was planted using seed from the best plant in field area D, seed of two plants from a salt tolerant synthetic of field area E, and seed of select plants from field areas F and G. Each seed lot comprised a half sib progeny of the selected female parental clone. Usually selection of the clones was based upon relatively high pyrethrin content in the year tested, as well as superior agronomic qualities, including plant vigor, planar flowers, synchronous flowering, and normal appearing flowers. Twenty-six parents were planted in three or more replicated thirty foot rows in a randomized complete block design constituting rows 1 to 45. Seed of a synthetic (CA 90 G SYN 1-13), obtained as a composite of all the seed harvested from rows 1 to 13 of field area G, was included as one entry, and in addition was planted in rows 46 to 54 as a nine row border at one end of field area H. Additionally, two rows of a high pyrethrin content sterile triploid plant from field area F (CA 87 F 4-101), were transplanted on the far side of the synthetic strips as rows 55 and 56.

Pyrethrin Analysis Methodology

Flowers are harvested in April at the ½ to ¾ disc floret open developmental stage. Flower samples are randomly collected and harvested onto ice and stored in darkness until transported from the field to the laboratory. Flower samples are then counted, weighed and stored at −70° C. The flowers are freeze dried in a lyophilizer for at least 24 hours, after which dry weights are taken. Flowers are then ground for 20 to 25 seconds in a grinder yielding a somewhat coarse yellow powder. Ground samples then are stored at −70° C. until extracted.

For pyrethrin extraction, 0.2 g of the ground flowers are added to a 50 ml culture tube, 10 ml of spectrograde hexane is added to the ground flowers and the tubes agitated slowly on a rotator for at least ten minutes. The tube is then emptied into a miracloth square and decanted into a second 50 ml tube. The ground flower cake is returned to the original tube, another 5 ml of hexane is added and the sample is again mixed on the rotator. The contents are again decanted into a miracloth square and the flower cake squeezed manually to expel all solvent into the second tube combining it with the first washing. The final volume of hexane flower extract is adjusted to 12 ml by evaporation under nitrogen, or by adding additional hexane. 3 ml of extract is pipetted into a serum collection vaccutainer tube and evaporated to dryness under nitrogen. The sample is stored under refrigeration until needed.

The evaporated sample residue is redissolved in 3 ml of HPLC grade methanol by vortexing for 30 seconds. The dissolved sample is filtered through a Gelman 0.45u Acrodisc syringe into a 5 ml culture tube and stored in a light-proof box under refrigeration until assayed.

Quantitative analysis of the pyrethrin content of the samples are carried out using a Varex Rosa-1 autosampler and injector interfaced with a Beckman dual pump 421A controlled, model 165 variable wavelength detector high performance liquid chromatograph, linked with a Beckman 427 microprocessor-controlled integrator. An Upchurch Scientific pre-column filled with Altech C-18 pre-column packing was mounted ahead of a Beckman Ultrasphere C-8 (or C-18) analytical column. The wavelength utilized was 229 nm, which was determined to be optimum to resolve the major pyrethrin components, based upon analysis of extinction coefficients of each of the six pyrethrin components across an array of wavelengths. The range of the instrument was set at 0.2 AUFS.

At the time of sample injection, the dual pump system was programmed to deliver a 50/50 HPLC grade acetonitrile/ double distilled, degassed water proportion. Two minutes after injection of the sample through a 10 ul loop, the gradient was programmed to increase at the rate of 1 and ⅔% acetonitrile per minute, for six minutes. The rate of change is then decreased to 0.93% acetonitrile per minute for 25 minutes. All pyrethrin peaks elute within 30 minutes. At the end of a 33 minute run, the acetonitrile is at 73.25%. A clean out step of 50/50 acetonitrile is programmed for 10 minutes between each sample injection. Time between automatic sample injections is 46 minutes.

All six pyrethrin components, i.e. Pyrethrin I, Pyrethrin II, Cinerin I, Cinerin II, Jasmolin I and Jasmolin II, are resolved as separate peaks, electronically integrated and expressed as area units at a given retention time (RT). Such integrations are highly repeatable over the several week period necessary for analysis of a year's flower sample data. One or more standard pyrethrin samples is injected every few samples, and the integrated areas of the individual pyrethrin components of this industry analyzed sample (Johnson Wax, East African Kenyan Board analyzed standard mixture 304) are used to quantify pyrethrins in Arizona grown clones.

Clone CA 87 F 4-101 (*Chrysanthemum cinerariaefolium* Vis. Arizona)

One of the distinct varieties produced by the above-described breeding program is an environmental stress tolerant, high pyrethrin content sterile triploid propagated in field area F, and is referred to as Clone CA 87 F 4-101 and designated *Chrysanthemum cinerariaefolium* Vis. Arizona. This clone was originally identified in a high pyrethrin producing clonal progeny in the field at the University of Arizona, Mararia Agricultural Center. A composite bulk of at least 2,500 seeds of at least twenty individual sister lines of Clone CA 87 F 4-101, was deposited on Nov. 30, 1995, at the American Type Culture Collection, 12201 Parklawn Drive, Rockville, Md. 20852, U.S.A., and was assigned the accession number ATCC 97352. The progenitors of Clone CA 87 F 4-101 were maintained by recurrent selection for environmental stress tolerance, high pyrethrin content, planar flowering habit, lodging resistance and ease of picking in the original test area at the University of Arizona, Campus Agricultural Center. This clone is the asexual propagule of a single plant (identified as CA 85 D 7-54) which was in turn selected from the half sib progeny of a plant identified as CA 83 A 7-13. Seven daughter clones (identified as CA 87 F 4-101; 102; 103; 104; 105; 106 and 107) of the single parent plant have been evaluated for agronomic phenotype consistency and pyrethrin content and quality.

Flowers of the daughter clones exhibit superior pyrethrin content when compared with the majority of other clones tested. High performance liquid chromatography analyses of hexane extracted, freeze dried flowers are presented in Table 1. The pyrethrin content of the clones, as measured by levels of Pyrethrin I (Chrysanthemum-monocarboxylic acid having the formula $C_{21}H_{28}O_3$ or the ester thereof), Pyrethrin II (Chrysanthemum-dicarboxylic acid having the formula $C_{22}H_{28}O_5$ or the ester thereof), Cinerin I, Cinerin II, Jasmolin I, Jasmolin II and the Pyrethrin I/Pyrethrin II ratios, meet or exceed that of the Authentic Kenyan pyrethrin standard. Table 2 presents agronomic characteristics of CA 85 D7-54 daughter clones which indicate markedly consistent plant height, flower diameter and flower weight between the daughter clones.

This characteristic is readily discernable in asexually propagated plant material. Clone CA 87 F 4-101 was found to be sterile and did not set viable seed even when pollinators were present. Thus, propagation is possible only through asexual means, and the daughter clones of CA 87 F 4-101 were all identical.

BRIEF DESCRIPTION OF THE DRAWINGS

"The file of this patent contains at least one drawing executed in color. Copies of this patent with color drawing (s) will be provided by the Patent and Trademark Office upon request and payment of the necessary fee."

The accompanying photographic drawings show typical inflorescence and foliage characteristics of CA 87 F 4-101 with the colors being as true as possible with such type of illustrations.

TABLE 1

| | | Peak areas at 229 nm × $10^2$ | | | |
|---|---|---|---|---|---|
| Compared | RT[1] | Authentic Kenyan STD 304 | RT | Clone CA 87 F 4-103 | RT | Clone CA 87 F 4-106 |
| Cinerin II | 18.9 | 70.9 | 18.7 | 39.8 | 18.7 | 37.5 |
| Pyrethrin II | 19.6 | 468.7 | 19.4 | 357.9 | 19.4 | 438.1 |
| Jasmolin II | 22.7 | 39.5 | 22.5 | 21.4 | 22.4 | 28 |
| Cinerin I | 28.8 | 73.9 | 28.5 | 47.6 | 28.4 | 46 |
| Pyrethrin I | 29.3 | 693.7 | 29 | 621.4 | 28.9 | 751.2 |
| Jasmolin I | 33 | 29 | 32.8 | 29 | 30.0 | 37 |
| Py I/Py II Ratio[2] | | 1.48 | | 1.74 | | 1.71 |

[1]RT — Retention Time (Min.)
[2]Not corrected for molar extinction coefficient differences

TABLE 2

| Clone I.D.[1] | Fresh wt./g/100 flowers | Dry wt./g/100 flowers | Flower Head diameter mm | Plant height[2] cm |
|---|---|---|---|---|
| CA 88 F 4-103 | 96 | 20 | 14.2 | 81 |
| CA 88 F 4-104 | 82 | 19 | 14.2 | 85 |
| CA 88 F 4-106 | 121 | 26 | 15.7 | 81 |
| CA 88 F 4-107 | 85 | 27 | 15.2 | 84 |

[1]Clones are daughter clones of CA 85 D7-54 and were harvested on different dates accounting for some morphological variance.
[2]Clones differed in overall crown size, also accounting for some morphological variance.

It has been found that the balance of pyrethrin isomers is under very strict genetic control and serves as a unique molecular fingerprint of each individual pyrethrin clone.

Figure 1:
FIG. 1 shows a row of a selected clone "Arizona" (CA 87 F 4-101) marked with a red flag, alongside rows of half sibs; and illustrates rows of half sibs; and illustrates the earlier, more profuse and uniform blooming, erect flower stems and uniform height as compared to half sib progeny depicted.
Figure 2:
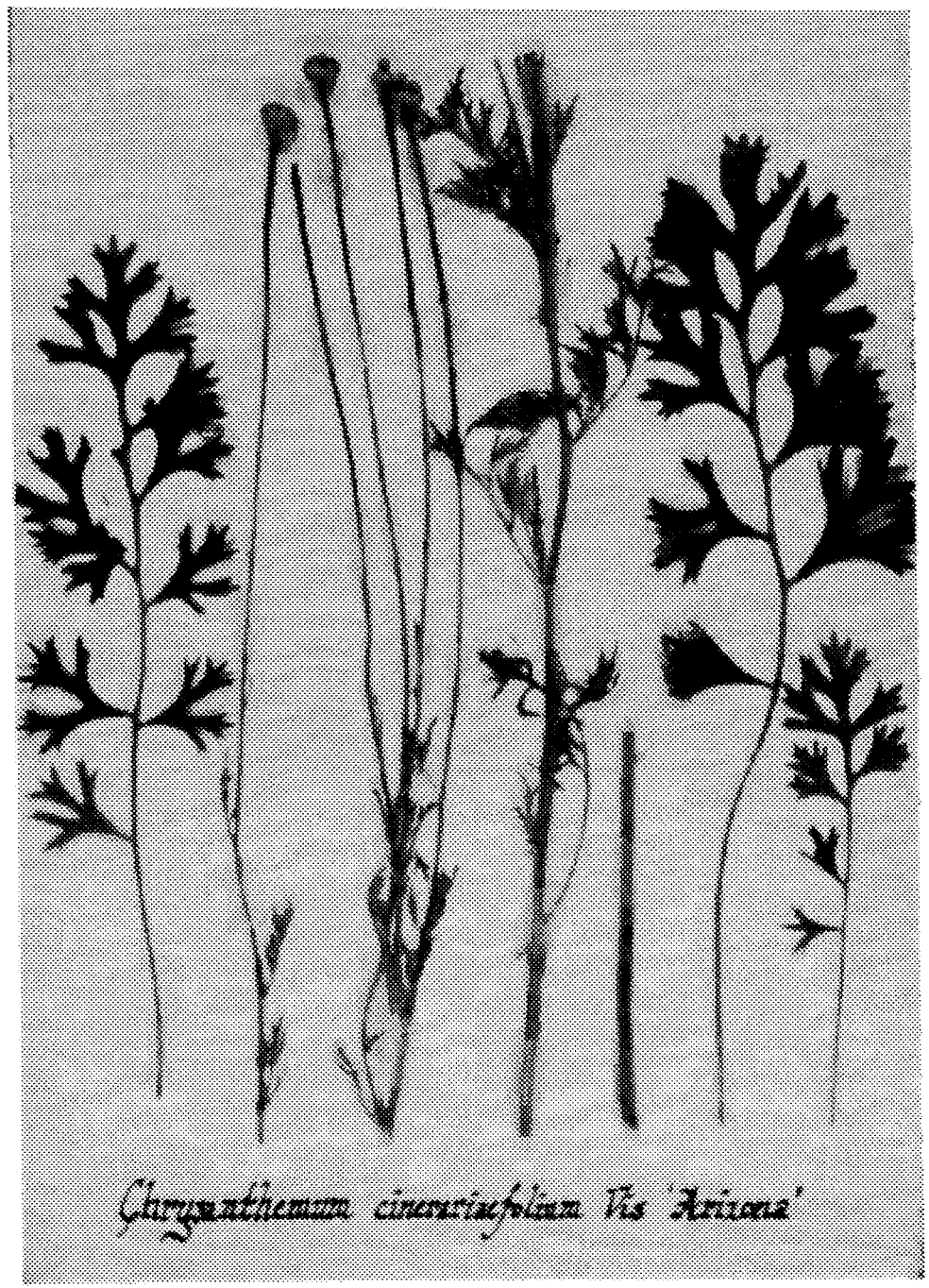
FIG. 2 illustrates a pressed herbarium specimen designated *Chrysanthemum cinerariaefolium* Vis. Arizona, showing a single mature flowering stem and typical leaves of this variety sectioned for convenience in pressing.
Figure 3:
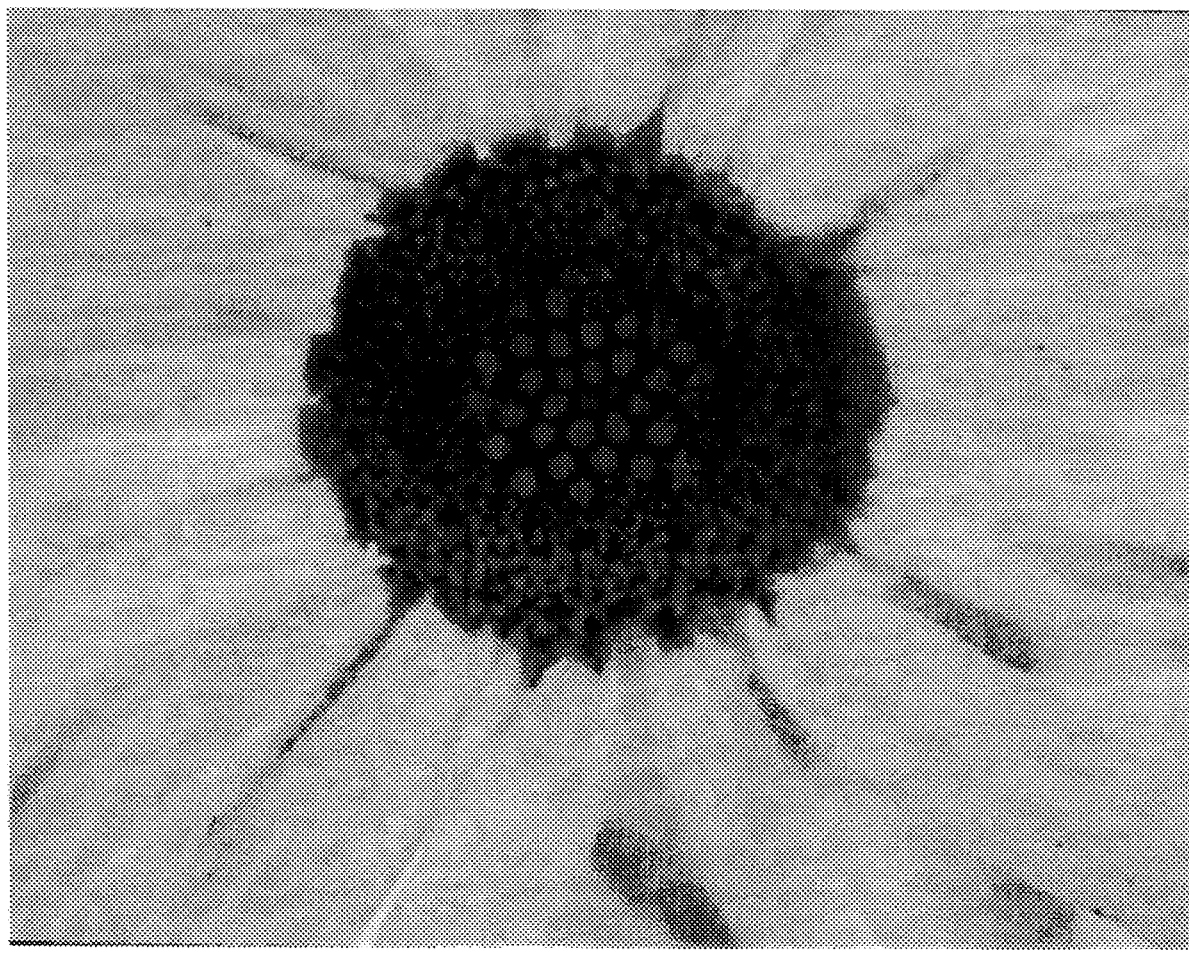
FIG. 3 illustrates a close-up of a single normal outcrossing fertile clone, which shows a halo of open florets noticeably raised above the surface of both the disc and ray florets such as that disclosed in Plant Patent No. 5,848 issued Jan. 6, 1987 to Bhat et al entitled "Chrysanthemum Plant Named Hypy."
Figure 4:
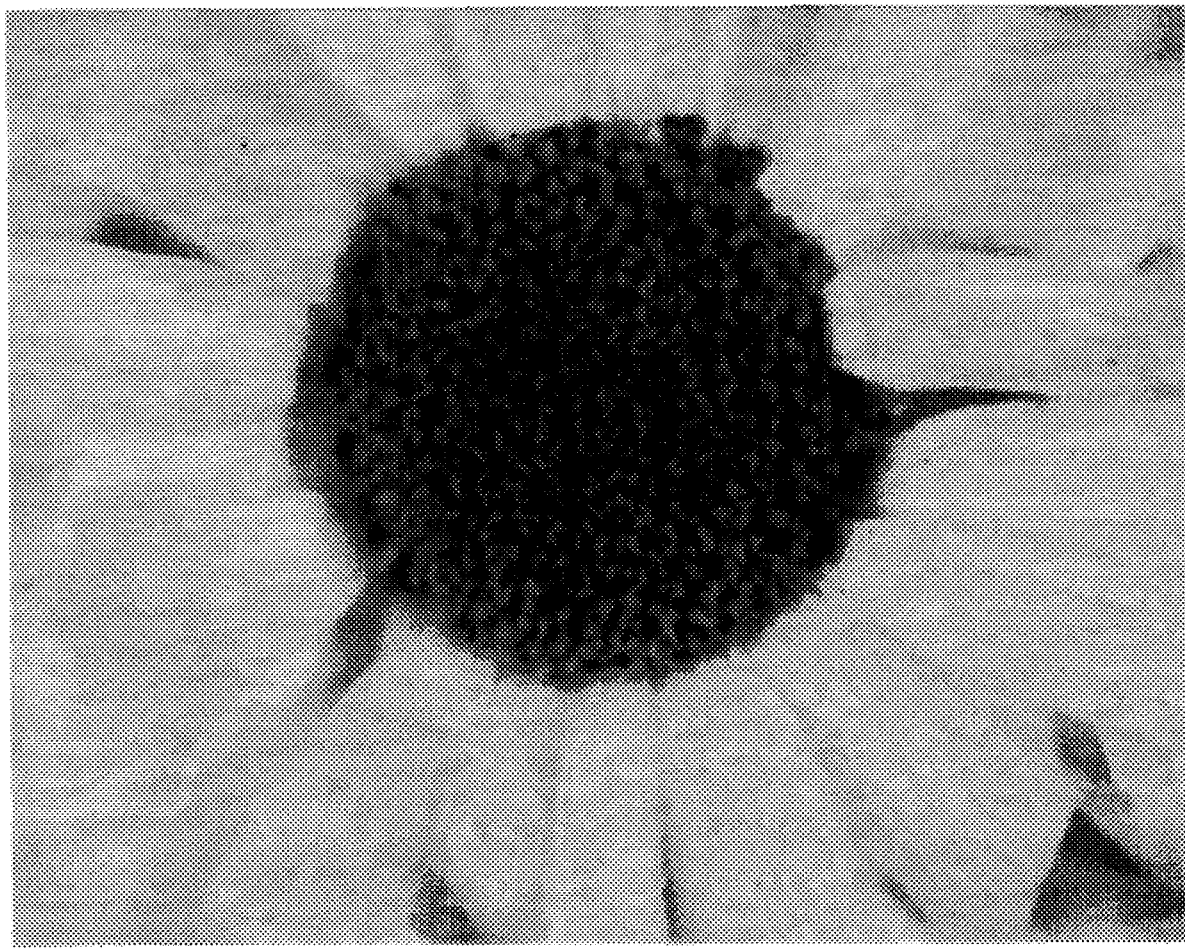

FIG. 4 illustrates a typical flower of CA 87 F 4-101 at the same developmental stage as that illustrated in FIG. 3, emphasizing the fully developed wide-open florets characteristic of this sterile clone.

Figure 5:

FIG. 5 illustrates a vertical section through the middle of the flower showing the shape of the receptacle and lengths of the ovary, tubular disk floret and petals of the ray floret.

Figure 6:
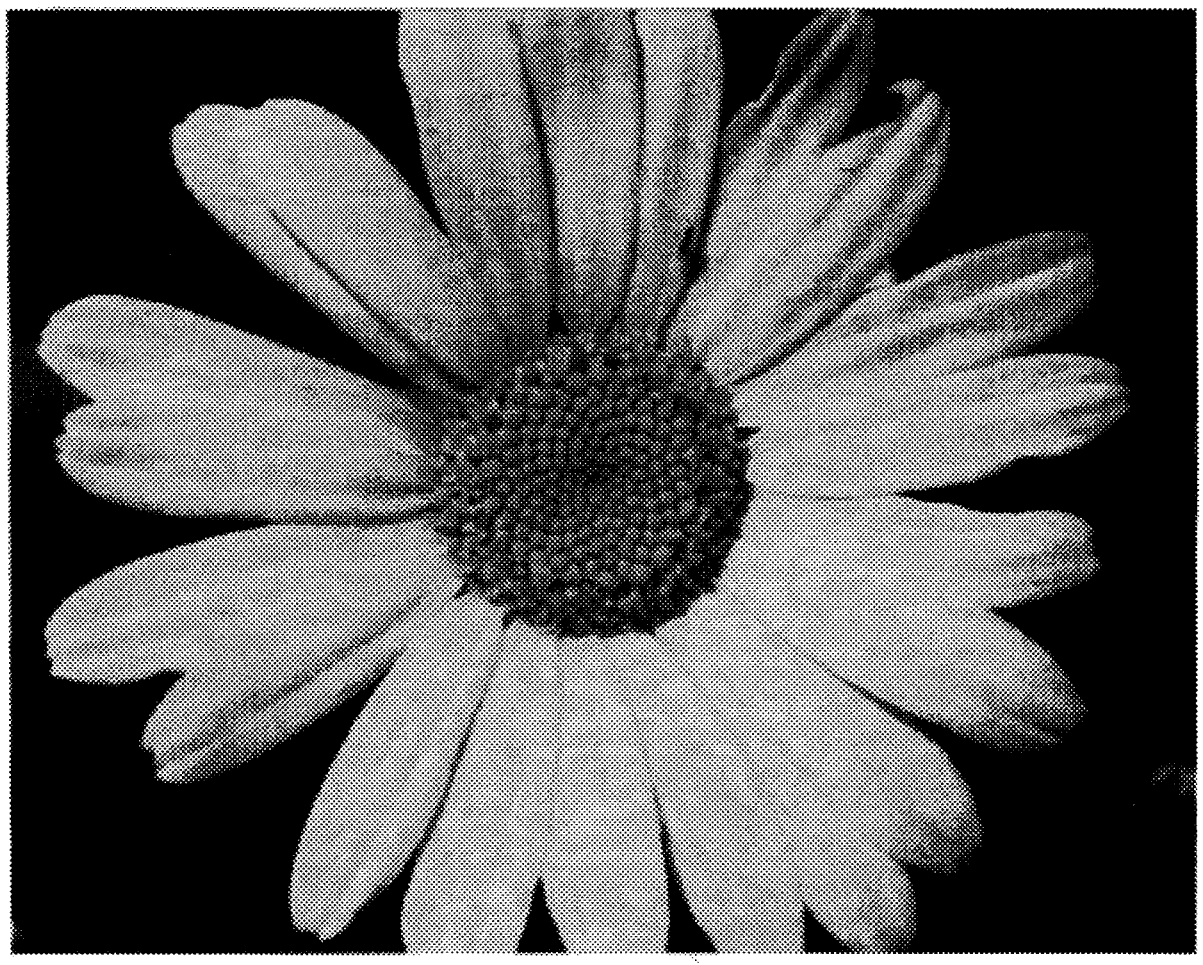

FIG. 6 illustrates a typical flower of *Chrysanthemum cinerariaefolium* Vis Arizona showing the florets and petals characteristic of this clone.

Clone CA 87 F 4-101 has very large flowers, prolific flowering and excellent vigor which correlate with good lodging resistance. In comparison with a normal, outcrossing fertile clone, which shows a halo of open florets noticeably raised above the surface of both the disc and ray florets, a typical flower of CA 87 F 4-101 at the same developmental stage exhibits a lack of developed open florets.(FIGS. 3 &

4). This clone blooms synchronously, and averages approximately 800 flowers per clone. Pyrethrin analysis of this clone, a sterile sister clone (designated F 4-117) and Kenyah Standard 304, show pyrethrin content of about 2% or greater as set forth in Table 3.

TABLE 3

| Year | Genotype | Py I/Py II Ratio | Percent Pyrethrins |
| --- | --- | --- | --- |
| 1986 | Kenyan Std. 304 | 1.42 | 2.00 |
| | D 7-54 | 1.18 | 2.09 |
| | D 7-19 | 1.33 | 1.83 |
| 1987 | Kenyan Std. 304 | 1.42 | 2.00 |
| | F 4-101 | 1.90 | 2.03 |
| | F 4-117[1] | n/a | n/a |
| 1988 | Kenyan Std. 304 | 1.36 | 2.00 |
| | F 4-101 | 1.56 | 1.95 |
| | F 4-117 | 1.61 | 2.25 |

[1]Flowers from Clone F-117 were not picked in 1987 due to small crown size.

Typical flowers of the clone contain considerably less pollen than the usual flower. Anthers contain what appear to be grayish, incompletely matured pollen grains. Some pollen looks fully developed and can sometimes be observed in a few anthers, depending upon the environment. Florets of the clone open more rapidly towards the center than the usual flowers. FIGS. 3 and 4 show flowers at the same relative time of development; the flower of the clone has completely opened florets, whereas the flower of the other lines have only partially opened florets. The clone is characterized by widely open florets, which are typical of sterile or partly sterile flowers from many species. The ray florets of the clone are believed to be completely sterile and the florets of the clone rapidly open from outside toward center. Two separate field plantings of seed from the clone have failed to germinate, whereas adjacent plantings of seed from other plants succeeded. Flowers of the clone have a strong scent which has been described by observers as an intense musty, aromatic chemical smell. Splitting the flower in half greatly intensifies the scent, so it does not appear to be a nectar volatile aroma. Flowers typically display from 22 to 27 petals, as illustrated in FIG. 6, compared to 19 to 22 of the typical pyrethrum flower. The clone has thicker stems which provide visually greater lodging resistance than other plants of similar height. Flowering stems of every other plant which are 90% as tall or taller than the clone fall over under field conditions. Peak bloom dates were Apr. 30, 1990, Apr. 25, 1989, Apr. 29, 1988 and Apr. 28, 1987. Plant heights of the clone averaged over 80 cm; flowers per plant averaged over 400 (with a maximum of over 500); typical plants ranged from 50 to 80 cm with an average of about 65 cm; flowers per plant ranged from 4 to approximately 450. A typical plant flower head diameter, not including petals, ranged from 9 mm to 14.3 mm with a mean of about 12.8 mm. Flower head diameter of the clone averaged about 15.03 mm. Flowers per stem of the clone averaged 5 (range of 1-10 with considerable variability); while the conventional plant averages 3 to 4 flowers on virtually every stem. The clone splits readily; the splits exhibit high field survival rates (over 90%) and a medium sized plant will usually yield 15 to 45 small to medium size splits, each with a sturdy, untwisted root system. All clones derived from the original plant bloomed in close synchrony, within 2 or 3 days, and reached peak flower opening rapidly, retained high pyrethrin content for at least two weeks and have agronomically favorable attributes of flowers borne at the same height, enabling the flowers to be mechanically harvested "once over".

The physical size of the clone relative to the great majority of other plants with similar genetic background, and other characteristics including sterility, plant height, flower diameter, petal member, stem diameter and number of flowers per stem, are all consistent with this plant being a triploid, which has been confirmed by root tip chromosome squashes.

It has been found that the clone exhibits optimum growth patterns in a wide range of elevations and stressful growing environments. Table 4 summarizes environmental responses of *Chrysanthemum cinerariaefolium* Vis. Arizona across a range of Arizona environments:

TABLE 4

| Location | Elevation (m) | Climatology and Agronomics |
| --- | --- | --- |
| Lakeside | 2137 | Snow cover protects crowns, cold/dry winters kill plants. |
| Elfrida | 1213 | Excellent survival; plants die back to crown in winter at temperatures down to about 9° F. |
| Safford | 900 | Plants under salt stress, perennial habit, small stature, lower pyrethrin levels. |
| Tucson | 714 | Near optimum location, high pyrethrin levels, good survival at temperatures in range of about 17° F. to about 111° F. |
| Tucson | 699 | Good environment, high soil nitrates burnt many transplanted splits. |
| Marana | 598 | More extreme temperatures in the range of about 15° F. to about 115° F. and high summer nighttime temperatures over 80° F. elicit crown rots. |
| Yuma | 50 | High summer temperatures and humidity cause fungus crown diseases and kill plants. |

In describing the colors, reference has been made to the book *R. H. S. Colour Chart*, published by the Royal Horticultural Society, London, England in association with the Flower Council of Holland.

INFLORESCENCE

A. Capitulum: Flat, daisy, diameter across face approximately 35-70 mm.

B. Corolla of Ray Florets: White, bright tonality.

C. Corolla of Disk Florets: Approximately orange-yellow 17A; (fresh colors); approximately yellow 7A to 13A (dried colors).

D. Reproductive Organs: Male flowers present in disk florets only and greatly reduced in function. Female flowers present in both disk and ray florets.

PLANT

A. Foliage:

Upper leaves: Approximately green 137C to 137D;

Midplant leaves: Green 137B to 137C

Lower leaves: Green 137A, 137B to 137C

Underside of leaves: Approximately green 147B to 147C.

The characteristics of Clone CA 87 F 4-101 are summarized as follows:

1. Stress tolerance to high heat and mild freezes.
2. Adaptation to Arizona latitude and elevation.
3. Pyrethrin content of 2% or more.
4. Balance of Pyrethrin I to Pyrethrin II (PyI/PyII ratio) close to that of preferred East African pyrethrins.

5. Sterile triploid.
6. Readily asexually propagated from splits.
7. Excellent plant vigor and spring regrowth.
8. Synchronous flowering. All flowers mature at nearly the same time, all daughter clones bloom together.
9. Vigorous and profuse flowering.
10. Planar flowering habit.
11. Large flowers exhibiting good flower form.
12. Plant color of medium green with a slight grey undertone.
13. Medium to large cut leaves.
14. Tall and erect phenotype.
15. 100 flower dry weight is about 23.0 grams.
16. Flowers are easily broken off stems, flowers normally retain no stem when picked.
17. Perennial habit
18. Good lodging resistance, due to large, stiff stems.

Synthetic Variety CA 87 F SYN 1

Another distinct variety produced by the breeding program described above is an environmental stress tolerant, high pyrethrin content fertile diploid which was obtained as seed from field area F, and is referred to as CA 87 F SYN 1. This variety consists of a composite of all of the seed harvested in 1987 and 1988 from the half sib progeny which were planted in rows 7 through 21 of field area F after being selected for environmental stress tolerance, high pyrethrin content, good lodging resistance and planar flowering habit. These rows were flanked on both sides by six rows (40 inch bed spacing) of similar or identical materials which served as guard rows to provide isolation from other field areas which might have inferior pollen.

Pyrethrin content was evaluated by replicated HPLC analyses of selected, representative plants representing the progeny of each seed source planted in each 30 foot block within the designated area of field area F. Average pyrethrin content is close to or in many cases exceeds the 2% pyrethrin/dry weight dilution of the Kenyan standard 304 extract.

The characteristics of synthetic variety CA 87 F SYN 1 are summarized as follows:

1. Stress tolerance to high heat and mild freezes.
2. Adaptation to Arizona latitude and elevation.
3. Pyrethrin content of about 2%.
4. A reasonable balance of Pyrethrin I to Pyrethrin II (PyI/PyII ratio); quite distinct, however, from East African pyrethrins.
5. Diploid
6. Good cross fertility to facilitate maintenance of seed stocks and seed increases, as judged by good seed germination.
7. These materials are progeny of plants in a recurrent program for ease of splitting, and so should be amenable to vegetative propagation also.
8. Low percentage of plants showing tendency to lodge.
9. Large percentage of plants exhibit planar flowering habit.
10. Nearly synchronous flowering. Maximum flowering intensity normally occurs over a two week period in April.
11. Most plants exhibit tall to mid-tall, erect phenotype.
12. Plant color of almost all plants is medium to mid-dark green deeply cut leaves small to medium in size.
13. Grown from seed, surviving plants in a stand show perennial growth habit and are well adapted to arid, irrigated Arizona agricultural environment.

Synthetic Variety CA 90 G SYN 1-13

A third distinct variety produced by the breeding program described above is an environmental stress tolerant, high pyrethrin content fertile diploid which was obtained as seed from field area G, and is referred to as CA 90 G SYN 1-13. This variety consists of a composite of all of the seed harvested from the half sib progeny which were planted in rows 1 through 13 of field area G after being selected for environmental stress tolerance, high pyrethrin content, good lodging resistance and planar flowering habit.

The characteristics of synthetic variety CA 90 G SYN 1-13 are similar to those reported above for synthetic variety CA 87 F SYN 1. The average pyrethrin content unexpectedly improved from 1.6% for the progenitor plants of the CA 90 G SYN 1-13 synthetic to 2.0% for the synthetic itself. Observation of the test plot strip showed that the unthrifty less vigorous or barren plants were failing to compete, when grown from seed in a dense stand. Also, hybrid vigor or heterosis of the seedlings likely contributed to the 0.4% advantage of the progeny.

Synthetic Variety CA 92 H SYN 1-45

A fourth distinct variety producedby the breeding program described above was obtained as seed from field area H, and is referred to as CA 92 H SYN 1-45. This variety consists of a composite of all of the seed harvested from the half sib progeny which were planted in rows 1 through 45 of field area H after being selected for high pyrethrin content, plant vigor, planar flowers, synchronous flowering and normal appearing flowers. Identification and pertinent data of the female parents of such half sib progeny are provided in Table 5. Based on the known characteristics of these female parents, the CA 92 H SYN 1-45 synthetic variety is expected to be an environmental stress tolerant, high pyrethrin content fertile diploid, with a predicted pyrethrin content around 2.5%. The synthetic seed, which can be reproduced throughout the estimated five seasons production life of field area H, have been planted in a 25 acre field, and pyrethrin content will be determined when they bloom in the spring of 1994.

In Table 5, all plants listed are diploids unless otherwise indicated. Also, those plants listed as "early", flower in mid-April as opposed to late-April, allowing the pyrethrin content to be maintained longer due to reduced temperature stress on the flowers.

TABLE 5

Female Parents of Plants Producing Synthetic Variety Seed CA 92 H SYN 1-45

| Parent | % pyrethrin | Mean flower diam. (mm) | Mean Petal count per flower | Mean Dry wt./ flower (g) | Information on plant |
|---|---|---|---|---|---|
| G18-104 | 2.21 | 13.33 | 22.7 | .32 | high pyrethrin and early |
| G9-19 | 2.89 | 14.50 | 20.8 | .36 | high pyrethrin and mid height |
| G13-136 | 2.07 | 15.00 | 20.3 | .43 | high pyrethrin |
| G6-122 | 2.47 | 14.67 | 21.5 | .40 | triploid, early high pyrethrin |
| F21-114 | 1.90 | 13.83 | | .40 | high pyrethrin |
| G18-2 | 2.30 | 13.83 | 22.3 | .35 | high pyrethrin and mid height |
| E5-28 | 1.86 | 13.67 | | .37 | early, salt tolerant |
| F27-63 | 2.36 | 13.67 | | .34 | high pyrethrin |
| G4-63 | 2.00 | 16.50 | 25.2 | .55 | triploid, early big flowers |
| G4-132 | 2.47 | | | | probable triploid high pyrethrin and early |
| G12-105 | 2.94 | 14.17 | 30.8 | .44 | high pyrethrin |
| G6-52 | 2.52 | 12.67 | 25.8 | .33 | high pyrethrin probable triploid |
| F12-4 | 1.91 | 12.83 | | .37 | high pyrethrin |
| F11-20 | 2.07 | 14.33 | | .36 | high pyrethrin |
| G12-103 | 2.44 | 13.00 | 23.8 | .38 | high pyrethrin |
| G10-137 | 2.50 | 16.67 | 29.7 | .60 | high pyrethrin big flowers |
| G20-129 | 2.17 | 12.25 | 21.7 | .27 | high pyrethrin |
| G21-98 | 2.33 | 12.25 | 20.8 | .32 | high pyrethrin and early |
| G5-62 | 1.73 | 11.67 | | .27 | high pyrethrin small, but prolific |
| G2-106 | 2.23 | 11.83 | 20.5 | .18 | high pyrethrin |
| G20-20 | 2.22 | 11.83 | 17 | .27 | high pyrethrin small, but prolific |
| E20-42 | 1.87 | 14.33 | | | short statured & salt tolerant |
| D8-81 | 1.74 | 13.17 | | .28 | short stature |
| F27-25 | 2.84 | 11.17 | | .29 | high pyrethrin |
| F9-132 | 2.92 | 13.50 | | .33 | high pyrethrin |
| F4-101 (clone) | 2.40 | 15.60 | | .44 | triploid & high pyrethrin |
| G1-13 | | | | | Synthetic variety- CA 90 G SYN 1-13 |

Pyrethrin content calculated based on mean of standards

One characteristic that appears to be common to all of the new and distinct varieties of Chrysanthemum cinerariaefolium plants in accordance with the present invention, is the presence on the plant's leaves of trichomes, or epidermal hairs. Such trichomes are known xeric adaptations which confer drought and heat stress tolerance to other plant species. By breaking the flow of air across the leaf surface in the wind, leaf hairs serve to restrict the loss of water from the leaf through transpiration. While it is not known for certain, it appears likely that the environmental stress tolerance exhibited by the Chrysanthemum cinerariaefolium varieties of the present invention, is at least to some extent related to the higher-than-normal trichome density per unit area of leaf surface characteristic of these varieties. Such trichome density has been observed to increase adjacent the midribs of the leaves of the plants of the present invention, and also to increase with increasing summer temperatures and decrease with decreasing winter temperatures.

In measuring trichome density per unit area of leaf surface, at least 3 unshaded leaves of similar age and stage of development are collected from each plant. Leaves are held in a zip lock bag with a small amount of water or wet unbleached kim towel to maintain turgor until measurements. A binocular dissecting microscope is used in conjunction with a measuring device either as part of the optics, or mounted beside the leaf on the stage. Sections of each leaf are scanned and one or more representative epidermal areas away from the midrib is selected. Trichomes in a 1 by 1 mm area are then counted. Trichomes in the "crease" area of the midrib are often more numerous, and a count of these is made unless the number of trichomes is too great. With a high density of trichomes (more than about 20–30) an estimate of trichome number is made. The leaves are then turned over and if deemed necessary, the bottom of the leaf is counted the same way.

The above-described procedure was used to measure the trichome density per square mm of leaf surface for six different plants selected from field area H. The results are reported in Table 6. The leaves were harvested on Feb. 4, 1993, and thus were winter leaves. For summer leaves, the trichome density away from the midrib would increase to close to the midrib trichome density.

TABLE 6

Trichome Density Per Square mm of Leaf Surface

| Clone | Ploidy | Field Position | Trichome Density[1] | Mean | Midrib Trichome Density[2] |
|---|---|---|---|---|---|
| F4-101 | Triploid | H55-1 | 6–10<br>5–10<br>8–12 | 8.5 | 70–100 |
| F4-101 | Triploid | H56-10 | 8–14<br>0–3<br>10–18 | 8.8 | 40–60 |
| G18-104 | Diploid | H16-90 | 4–12<br>2–6<br>2–4 | 5 | 4–20 |
| G18-104 | Diploid | H1-1 | 0–4<br>8–12<br>4–8 | 6 | 0–12 |
| G12-105 | Diploid | H38-61 | 0–2<br>2–6<br>0–2 | 2 | 0–12 |
| G1 to 13 | Diploid | H53-90 | 0–1<br>4–8<br>0–2 | 2.5 | 4–12 |

[1]Average range of observed trichomes from selected areas away from the midrib on each of three individual leaves.
[2]Estimated range.

The new and distinct varieties of *Chrysanthemum cinerariaefolium* plants in accordance with the present invention, are also capable of being propagated in tissue culture from various propagating material, including seed, cut meristems and cut stem and leaf pieces, by standard tissue culture techniques well known in the art.

The first step in carrying out the tissue culture procedure is the generation of pyrethrum callus from the propagating material. When the pyrethrum callus is initiated from seed, the seed is first surface sterilized with bleach and then germinated on sterile water agar plates. The sterilization is carried out by tying the seed in a cheesecloth bag and immersing the bag in full strength bleach for about 20 minutes while stirring. The bag allows the bleach solution to freely wash the seed, and also allows easy removal of the seed from the solution. Sterile techniques are thereafter used for handling the seed. The seeds in the cheesecloth bag are removed from the bleach solution with sterile tweezers and rinsed three times in sterile deionized water. The cheesecloth bag is then cut open with a sterile scalpel, and the seeds are removed therefrom and spread out on sterile water agar plates for germination, which usually takes approximately a week.

The sterile water agar plates used for germinating the seed are typically prepared beforehand by adding 10 grams of agar to 1 liter of deionized water and autoclaving for 20 minutes. The resulting water agar medium is then poured out into plates using sterile technique, and the plates are parafilmed shut and stored in a cooler prior to use.

After the seed has germinated, the seedling is cut into several approximately 3–4 mm pieces and spread out onto plates of a suitable pyrethrum tissue culture medium, such as described below. The plates are then parafilmed shut around the edges. Callus will begin to generate from the cut ends of the pieces of tissue in 1 to 3 weeks.

When cut meristems or cut stem or leaf pieces are utilized as the source for callus production, these tissues require a gentler sterilization treatment than that described above for seed. A more suitable sterilization treatment for these tissues is a 10 to 15 second rinse in 70% ethanol, followed with several sterile deionized water rinses.

For best results, the callus should be transferred to fresh medium about every 1 to 2 weeks. The transfer is effected by taking an approximately marble sized piece of callus with a sterile scoop, and transferring it to a fresh plate of medium, which is then parafilmed shut around the edges. Sterile technique in a laminar air flow hood is used while transferring the callus.

Once the pyrethrum callus has been generated, the sterile tissues are then separated therefrom as individual cells, sorted by size, and placed into liquid suspension cultures to form somaclonal progeny, following standard tissue culture techniques well known in the art.

The following tissue culture medium formulation has been found to be particularly suitable for use in pyrethrum tissue culture in accordance with the present invention. The amounts listed will make 1 liter of medium.

| | |
|---|---|
| Double distilled water | 700 ml |
| Add in the following order with constant stirring: | |
| Major Elements (10 × concentrate solution)* | 150 ml |
| Chelated Iron (100 × concentrate solution) | 15 ml |
| MS Minor Elements (100 × concentrate solution)** | 15 ml |
| Sucrose | 30 g |
| Hormones: | |
| 1. 6-BA (6-benzylaminopurine) | 1 ml |
| 2. 2,4-D (2,4-Dichlorophenoxy Acetic Acid) | .25 ml |
| 3. Glycine | 1 ml |
| MS vitamins** (100 × concentrate solution) | 10 ml |
| Adjust pH to 5.7 with NaOH or HCl | |
| Add double distilled water to make 1 liter. | |
| Agar | 10 g |
| Mix with heat until agar melts, autoclave for 20 minutes, and in the laminar air flow hood, pour into sterile petri plates, and parafilm when cool. | |

*Modifications to the basic Murashige and Skoog for major salts have been made to the major salts for pyrethrum tissue culture as follows: Half of the standard amount on $NH_4NO_3$ was used. All other amounts remained as specified by Murashige and Skoog.
**These were standard Murashige and Skoog formulas and amounts for standard MS media.

What is claimed is:

1. A *Chrysanthemum cinerariaefolium* plant exhibiting environmental stress tolerance to a growing climate characterized by temperature extremes as low as about 17° F. and as high as about 115° F., said plant being capable of producing flowers having an endogenous pyrethrin content of at least 1.5% by weight of dried flowers while being grown under said growing climate.

2. The *Chrysanthemum cinerariaefolium* plant of claim 1, wherein said pyrethrin content is at least 2.0% by weight of dried flowers.

3. The *Chrysanthemum cinerariaefolium* plant of claim 1, wherein said flowers have a pyrethrin I to pyrethrin II ratio of at least 1.

4. The *Chrysanthemum cinerariaefolium* plant of claim 1, wherein said plant exhibits synchronous and planar flowering habit and erect growth with resistance to lodging.

5. The *Chrysanthemum cinerariaefolium* plant of claim 1, wherein said plant has leaves having epidermal trichomes.

6. The *Chrysanthemum cinerariaefolium* plant of claim 5, wherein the trichome density per unit area of leaf surface increases adjacent the midrib of the leaf.

7. The *Chrysanthemum cinerariaefolium* plant of claim 5, wherein the trichome density per unit area of leaf surface increases with increasing summer temperatures and decreases with decreasing winter temperatures.

8. The *Chrysanthemum cinerariaefolium* plant of claim 1, wherein said plant is a triploid.

9. The *Chrysanthemum cinerariaefolium* plant of claim 1, wherein said plant is a diploid.

10. The *Chrysanthemum cinerariaefolium* plant of claim 9, wherein said plant is capable of producing seed, said seed being capable of germinating into a progeny plant, said progeny plant also exhibiting environmental stress tolerance to a growing climate characterized by temperature extremes as low as about 17° F. and as high as about 115° F., said progeny plant also being capable of producing flowers having an endogenous pyrethrin content of at least 1.5% by weight of dried flowers while being grown under said growing climate.

11. The *Chrysanthemum cinerariaefolium* plant of claim 1, wherein said plant exhibits environmental stress tolerance to saline-sodic soil in an arid, irrigated agricultural environment.

12. A *Chrysanthemum cinerariaefolium* seed capable of germinating into a plant, said plant exhibiting environmental stress tolerance to a growing climate characterized by temperature extremes as low as about 17° F. and as high as 115° F., said plant being capable of producing flowers having an endogenous pyrethrin content of at least 1.5% by weight of dried flowers while being grown under said growing climate.

13. The *Chrysanthemum cinerariaefolium* seed of claim 12, wherein said pyrethrin content is at least 2.0% by weight of dried flowers.

14. The *Chrysanthemum cinerariaefolium* seed of claim 12, wherein said flowers have a pyrethrin I to pyrethrin II ratio of at least 1.

15. The *Chrysanthemum cinerariaefolium* seed of claim 12, wherein said plant exhibits synchronous and planar flowering habit and erect growth with resistance lodging.

16. The *Chrysanthemum cinerariaefolium* seed of claim 12, wherein said plant has leaves having epidermal trichomes.

17. The *Chrysanthemum cinerariaefolium* seed of claim 16, wherein the trichome density per unit area of leaf surface increases adjacent the midrib of the leaf.

18. The *Chrysanthemum cinerariaefolium* seed of claim 16, wherein the trichome density per unit area of leaf surface increases with increasing summer temperatures and decreases with decreasing winter temperatures.

19. The *Chrysanthemum cinerariaefolium* seed of claim 12, wherein said plant is a triploid.

20. The *Chrysanthemum cinerariaefolium* seed of claim 12, wherein said plant is a diploid.

21. The *Chrysanthemum cinerariaefolium* seed of claim 12, wherein said plant exhibits environmental stress tolerance to saline-sodic soil in an arid, irrigated agricultural environment.

22. Propagating material of the *Chrysanthemum cinerariaefolium* plant of claim 1.

23. Somaclonal progeny produced by tissue culture of the propagating material of claim 22, said somaclonal progeny also exhibiting environmental stress tolerance to a growing climate characterized by temperature extremes as low as about 17° F. and as high as about 15° F., said somaclonal progeny also being capable of producing flowers having an endogenous pyrethrin content of at least 1.5% by weight of dried flowers while being grown under said growing climate.

* * * * *